United States Patent
Morris

(10) Patent No.: US 7,224,461 B2
(45) Date of Patent: May 29, 2007

(54) METHOD FOR DETERMINING MODIFICATIONS TO SEMICONDUCTOR OPTICAL FUNCTIONS

(75) Inventor: Stephen J. Morris, Shrewsbury (GB)

(73) Assignee: Therma-Wave, Inc., Fremont, CA (US)

(*) Notice: Subject to any disclaimer, the term of this patent is extended or adjusted under 35 U.S.C. 154(b) by 445 days.

(21) Appl. No.: 10/847,423

(22) Filed: May 17, 2004

(65) Prior Publication Data

US 2004/0252306 A1 Dec. 16, 2004

Related U.S. Application Data

(60) Provisional application No. 60/475,919, filed on Jun. 5, 2003, provisional application No. 60/504,890, filed on Sep. 22, 2003.

(51) Int. Cl.
*G01N 21/55* (2006.01)

(52) U.S. Cl. ..................................................... 356/445

(58) Field of Classification Search ................ 356/445, 356/73, 368, 369
See application file for complete search history.

(56) References Cited

U.S. PATENT DOCUMENTS

| 5,796,983 | A | 8/1998 | Herzinger et al. | 395/500 |
|---|---|---|---|---|
| 5,798,837 | A | 8/1998 | Aspnes et al. | 356/369 |
| 6,485,872 | B1 * | 11/2002 | Rosenthal et al. | 430/30 |
| 6,862,095 | B2 * | 3/2005 | Horie | 356/445 |
| 7,110,640 | B2 * | 9/2006 | LoCascio et al. | 385/27 |
| 7,110,912 | B1 * | 9/2006 | Tiwald | 702/170 |

OTHER PUBLICATIONS

J.-Th. Zettler et al., "High precision UV-visible-near-IR Stokes vecter spectroscopy," *Thin Solid Films*, vol. 234 (1993), pp. 402-407.

J. Leng et al., "Analytic representations of the dielectric functions of materials for device and structural modeling," *Thin Solid Films*, vol. 313-314 (1998), 132-136.

C. Ygartua et al., "Characterization of Epitaxial Silicon Germanium Thin Films by Spectroscopic Ellipsometry," *ICSE Conference May 1997*, 7 pages in length.

L. Vina et al., "Effect of heavy doping on the optical properties of the bank structure of silicon," *Physical Review B*, vol. 29, No. 12, Jun. 15, 1984, pp. 6739-6751.

D.E. Aspnes et al., "Dielectric properties of heavily doped crystalline and amorphous silicon from 1.5 to 6.0 eV," *Physical Review B*, vol. 29, No. 2, Jan.15, 1984, pp. 768-779.

(Continued)

*Primary Examiner*—Gregory J. Toatley, Jr.
*Assistant Examiner*—Isiaka O. Akanbi
(74) *Attorney, Agent, or Firm*—Stallman & Pollock LLP

(57) ABSTRACT

A method for modeling the complex refractive index of doped, strained or ultra-thin semiconductors starts with a model for a standard bulk material which may be in any form such as a pre-existing lookup table, a dispersion model derived from an effective medium approximation (EMA) or a critical point (CP) model. The modeling method perturbs the $\in_2$ curve of the bulk material by enhancing, suppressing or shifting the strong features of the curve. A Kramers-Kronig transformation is then applied to the $\in_2$ perturbation to obtain the corresponding perturbation to the $\in_1$ curve. The combination of the perturbed $\in_2$ curve and the correspondingly perturbed $\in_1$ curve are then used to obtain the complex dielectric function or complex refractive index of the modified material.

8 Claims, 12 Drawing Sheets

OTHER PUBLICATIONS

C.C. Kim et al., "Modeling the optical dielectric function of semiconductors: Extension of the critical-point parabolic-band approximation," *Physical Review B*, vol. 45, No. 20, May 15, 1992-II, pp. II 749-II 767.

F.L. Terry, Jr., "A modified harmonic oscillator approximation scheme for the dielectric constants of $Al_zGA_{1-x}As$," *J. Appl. Phys.*, vol. 70, No. 1, Jul. 1, 1991, pp. 409-417.

E. Erman et al., "Optical properties and damage analysis of GaAs single crystals partly amorphized by ion implantation," *J. Appl. Phys.*, vol. 56, No. 10, Nov. 15, 1984, pp. 2664-2671.

D.E. Aspnes et al., "Optical properties of $Al_xGa_{1-x}As$," *J. Appl. Phys.*, vol. 60, No. 2, Jul. 15, 1986, pp. 754-767.

P.G. Snyder et al.,"Modeling $Al_xGa_{1-x}As$ optical constants as funcions of composition," *J. Appl. Phys.*, vol. 68. No. 11, Dec. 1, 1990, pp. 5925-5926.

U. Schmid et al., "Optical transistions in strained Ge/Si superlattices," *Physical ReviewB*, vol. 45, No. 12, Mar. 15, 1992-II, pp. 6793-6801.

D.V. Lang et al., "Measurement of the band gap of $Ge_xSi_{1-x}$/Si strained-layer heterstructures," *Appl. Phys. Lett.*, vol. 47, No. 12, Dec. 15, 1985, pp. 1333-1335.

A.P. Prudinikov et al., treatise "Integrals and series," *published under license by Gordon and Breach Science Publishers S.A.* (© 1986), section entitled "Indefinite Integrals," pp. 40-41.

* cited by examiner

METHOD FOR DETERMINING MODIFICATIONS TO SEMICONDUCTOR OPTICAL FUNCTIONS

PRIORITY CLAIM

The present application claims priority to U.S. Provisional Patent Application Ser. No. 60/475,919, filed Jun. 5, 2003, and U.S. Provisional Patent Application Ser. No. 60/504,890, filed Sep. 22, 2003, both of which are incorporated in this document by reference.

TECHNICAL FIELD

The subject invention relates to optical devices used to non-destructively characterize thin films on semiconductor wafers. In particular, the present invention relates to techniques for modeling changes induced in the dielectric properties of semiconductor materials as a result of effects such as doping, strain or confinement so that measurements of these effects may be undertaken with a suitable optical apparatus. Furthermore, the present invention facilitates the modeling of dielectric properties simultaneously with respect to these changes and other changes, for example those due to varying alloy composition in SiGe or other compound semiconductors.

BACKGROUND OF THE INVENTION

As geometries continue to shrink, manufacturers of semiconductor devices need continually to improve the control of their manufacturing processes. At the same time as layer thicknesses and feature sizes decrease, so also the complexity of the structures to be measured and of the materials within those structures increases. In many cases it becomes necessary to characterize material properties that were previously neglected to the first order, or to find new methods of characterization where the limitations of previous methods have become significant obstacles to progress.

For a long time, optical techniques have been favored for measuring the thicknesses and other properties of transparent or semi-transparent films. Techniques of this type, known generally as optical metrology, operate by illuminating a sample with electromagnetic radiation (typically referred to as a probe beam) and then detecting and analyzing the reflected energy. They have the advantage of being non-contact and non-destructive, and they can provide high throughput and almost arbitrarily small measurement spot sizes (ultimately limited only by the wavelength of the probe beam).

Two broad classes of optical technique commonly used in this context are Reflectometry and Ellipsometry. In Reflectometry, changes in the amplitude of the reflected light are measured, usually as a function of either the angle of incidence or the wavelength of the probe beam. The latter case is more usually referred to as Spectrophotometry, or just Spectrometry. In Ellipsometry, the change in polarization of the probe beam is measured, usually by quantifying the difference in sample reflectance between s-polarized light (in which the electric field vector is perpendicular to the plane of incidence) and p-polarized (in which it is parallel to the plane). This too can be carried out as a function of either the angle of incidence or the wavelength of the light.

A variety of such techniques can be combined on a common platform, as is the case with the Opti-Probe® tool offered by the Assignee and conceptually described in U.S. Pat. No. 5,798,837 which is incorporated in this document by reference. In particular, this tool combines a proprietary method of single-wavelength Reflectometry, a method of Spectrophotometry and three complementary methods of Ellipsometry which can be employed singly or in any combination.

In addition to film thickness, techniques of this type may be used to analyze a wide range of attributes including refractive index and extinction, crystallinity, composition, porosity and roughness. To measure the doping level in a semiconductor material, however, it has often been necessary to resort to a non-optical technique such as Secondary Ion Mass Spectrometry (SIMS) or resistivity modeling.

An optical technique does not of course measure the material attributes directly, but by comparing the reflected light from the sample with the calculated reflectance of a "model filmstack". The computer program controlling this process is customarily referred to as a "recipe", and the aim of the recipe is to find the model that is the most faithful possible representation of the sample. This is done by regressively optimizing the parameters that describe the model filmstack until there is the closest possible correspondence between the calculated reflectance of the model and the actual reflectance of the sample. The outputs from the recipe are the parameters describing the model filmstack. It is customary to quantify the closeness of the correspondence between the calculated and actual reflectances by means of a "Residual" or "Goodness of Fit" (GOF) parameter.

It can therefore be seen that the success of such an approach depends upon being able to choose parameters that accurately represent the physical attributes of the sample. For any film layer, these parameters include thickness as well as dielectric properties of the material. Typically, these parameters are expressed in terms of the sample's optical dispersion; that is, the manner in which the complex refractive index ($N = n - ik$) or complex dielectric function ($\in = \in_1 + i\in_2$) varies as a function of the wavelength or (equivalently) photon energy of the light. There is a large class of models that enable these functions to be represented parametrically. Simplest of all is the lookup-table approach, in which case the values of n and k (or $\in_1$ and $\in_2$) at each wavelength are effectively independent parameters, but it is usual to seek to reduce the number of parameters using a mathematical formula of some sort. The most familiar is the Cauchy model, whereby n and k are represented as an expansion of the form $$n(\lambda) = n_0 + \frac{n_1}{\lambda^2} + \frac{n_2}{\lambda^4} + \cdots \qquad (1)$$

$$k(\lambda) = k_0 + \frac{k_1}{\lambda^2} + \frac{k_2}{\lambda^4} + \cdots$$

However, this still suffers from the drawback that n and k are regarded as being independent functions, whereas in fact they are not: they are related via the Kramers-Kronig transform, viz.

$$n + ik = \sqrt{\varepsilon_1 + i\varepsilon_2} \qquad (2)$$

$$\varepsilon_1(E_0) = 1 + \int_0^\infty \frac{E\varepsilon_2(E)}{E^2 - E_0^2} dE \qquad (3)$$

By far the most satisfactory models are those that explicitly satisfy this condition, but even of these there are a great many. Most involve the use of ensembles of oscillators, either of classical Lorentz form (see, for example, C. Ygartua and M. Liaw, "Characterization of epitaxial silicon germanium thin films by spectroscopic ellipsometry", Thin Solid Films 313–314, 237 (1998)) or of modified harmonic form (see, for example, J. Leng, J. Opsal, H. Chu, M. Senko and D. E. Aspnes, "Analytical representations of the dielectric functions of materials for device and structural modeling", Thin Solid films 313–314, 132 (1998), C. C. Kim, J. W. Garland, H. Abad and P. M. Raccah, "Modeling the optical dielectric function of semiconductors: extension of the critical-point parabolic-band approximation", Phys. Rev. B45, 11749 (1992), or F. L. Terry, "A modified harmonic oscillator approximation scheme for the dielectric constants of AlxGa1-xAs", J. Appl. Phys. 70, 409 (1991)). Models also exist to combine two or more pre-existing Kramers-Kronig consistent dispersions into a resultant dispersion, either via an effective-medium approximation (EMA—see, for example, M. Erman, J. B. Theeten, P. Chambon, S. M. Kelso and D. E. Aspnes, "Optical properties and damage analysis of GaAs single crystals partly amorphized by ion implantation", J. Appl. Phys. 56, 2664 (1984) which, incidentally, also presents an early version of the harmonic oscillator model) or an Alloy model (see, for example, D. E. Aspnes, S. M. Kelso, R. A. Logan and R. Bhat, "Optical properties of AlxGa1-xAs", J. Appl. Phys. 60, 754 (1986) and P. G. Snyder, J. A. Woollam, S. A. Alterovitz and B. Johs, "Modeling AlxGa1-xAs optical constants as functions of composition", J. Appl. Phys. 68, 5925 (1990)).

However, none of these techniques are naturally suited to modeling the specific effects that doping has upon the dielectric functions of semiconductors. The presence of dopants can have a significant effect on the dielectric response of semiconductor materials. To illustrate, FIG. 1 shows measured values for $\varepsilon_2$ plotted as a function of photon energies for Silicon. As shown, the $\varepsilon_2$ curve has two strong features. These occur at photon energies of ~3.4 eV and 4.2 eV and are denoted "E1" and "E2" respectively. As described in "Effects of Heavy Doping on the Optical Properties and the Band Structure of Silicon" (L. Viña and M. Cardona, Phys. Rev. B29, 6739 (1984), and contemporaneously by D. E. Aspnes, A. A. Studna and E. Kinsbron in "Dielectric properties of heavily doped crystalline and amorphous silicon from 1.5 to 6.0 eV", Phys. Rev. B29, 768 (1984)) the principal effect of doping on the optical properties of these materials is to suppress, and at higher doping levels shift, the E1 and E2 features (with the effect on the E1 feature typically being more profound). This is verified by modeling the dielectric function of a doped epitaxial Si film (with a Boron content of ~2.5×10$^{19}$ cm$^{-3}$) on a nominally undoped Si substrate, as also shown in FIG. 1. The limitations of the existing models are these: firstly, in the oscillator methods each feature in the $\varepsilon_2$ curve is made up of contributions from more than one oscillator, so it is difficult to correlate subtle changes in the shapes of features with specific oscillator parameters. Secondly, because of this "nonlocal" nature of oscillator models, the ability to fit the shape of a feature in one part of the spectrum where data is available may be hindered by the unavailability of data from another part of the spectrum. A practical example of this is when a SiGe layer buried under an epitaxial Si cap must be measured, as the Si cap is opaque to wavelengths of light in the DUV region (photon energies above ~3 eV) and so no information about the SiGe is available in this range (which includes the positions of both the E1 and E2 peaks). The method of Herzinger et al., in U.S. Pat. No. 5,796,983, would seem to address the first of these limitations but not the second. Alloy or EMA models could be used to interpolate between different dispersion curves corresponding to known levels of doping, but this could only work if all other material properties (e.g. Germanium content in a SiGe film) could be assumed constant. Moreover, the component models with known doping levels would need to exist for the particular combination of other material properties being studied, and this would not generally be the case.

Other effects that can cause similar subtle changes to the dielectric functions of the film are strain (see for example U. Schmid, J. Humlíček, F. Lukeš, M. Cardona, H. Presting, H. Kibbel, E. Kasper, K. Eberl, W. Wegscheider and G. Abstreiter, "Optical transitions in strained Ge/Si superlattices", Phys. Rev. B45, 6793 (1992)) and (in very thin films, of the order of tens of nanometers or less) quantum confinement (see, for example, D. V. Lang, R. People, J. C. Bean and A. M. Sergent, "Measurement of the band gap of Ge$_x$Si$_{1-x}$/Si strained-layer heterostructures", Appl. Phys. Lett. 47, 1333 (1985)).

There is therefore a need for a technique that can decouple these subtle effects from the complex overall structure of the semiconductor's dielectric functions. Such a technique should be able to distinguish changes in, for example, doping level from other things that may affect the material's optical properties (such as changing Ge content in a SiGe film), extract such information even when optical data is only available from a limited wavelength range (such as, for example, a doped SiGe layer buried under an epitaxial Si cap), and enable an efficient computational algorithm to implement the technique in the context of real-time production measurement. The present invention provides such a technique.

SUMMARY

The present invention can be encapsulated in the assertion that the effect of changes such as doping, strain or confinement upon the dielectric function of a semiconductor material can be separated out as a perturbation upon the dielectric function of the bulk material. Specifically, recapping equation (3) from the previous section, $$\varepsilon_1(E_0) = 1 + \int_0^\infty \frac{E\varepsilon_2(E)}{E^2 - E_0^2} dE \qquad (3)$$

the functions $\varepsilon_1'(E)$ and $\varepsilon_2'(E)$ for the modified material can be represented as superpositions of the functions $\varepsilon_1(E)$ and $\varepsilon_2(E)$ for the corresponding bulk material plus perturbations $\Delta\varepsilon_1(E)$ and $\Delta\varepsilon_2(E)$. Because the dielectric functions of the modified and bulk material must both alike satisfy equation (3), we can write $$\varepsilon_1'(E_0) = 1 + \int_0^\infty \frac{E\varepsilon_2'(E)}{E^2 - E_0^2} dE$$

$$\Rightarrow \varepsilon_1(E_0) + \Delta\varepsilon_1(E_0) = 1 + \int_0^\infty \frac{E(\varepsilon_2(E) + \Delta\varepsilon_2(E))}{E^2 - E_0^2} dE$$

and by subtracting both sides of equation (3), $$\Delta\varepsilon_1(E_0) = \int_0^\infty \frac{E\Delta\varepsilon_2(E)}{E^2 - E_0^2} dE \qquad (4)$$

In general, it will be possible to obtain the values of the functions $\varepsilon_1(E)$ and $\varepsilon_2(E)$ for the bulk material from some other source, such as pre-existing lookup table (for a single-element semiconductor such as Silicon) or an Effective-Medium or Alloy model (for an alloy semiconductor such as SiGe). Therefore, it is only necessary to parameterize the function $\Delta\epsilon_2(E)$ and optimize the resulting parameters in order to be able to obtain the whole dielectric function of the modified material and, by correlation with the parameters, the nature of the modification (e.g., the doping level or amount of strain).

It may be further noted that by using the dielectric functions from the bulk material, which by definition must satisfy equation (3), the need to do the Kramers-Kronig integration from zero to infinity is allayed. There is freedom to parameterize the function $\Delta\epsilon_2(E)$ in such a way as it is equal to zero at all wavelengths away from the vicinities of the strong features being modified, or, alternatively, in such a way that the integration from zero to infinity may be done analytically.

DETAILED DESCRIPTION OF THE PREFERRED EMBODIMENTS

Figure 1:
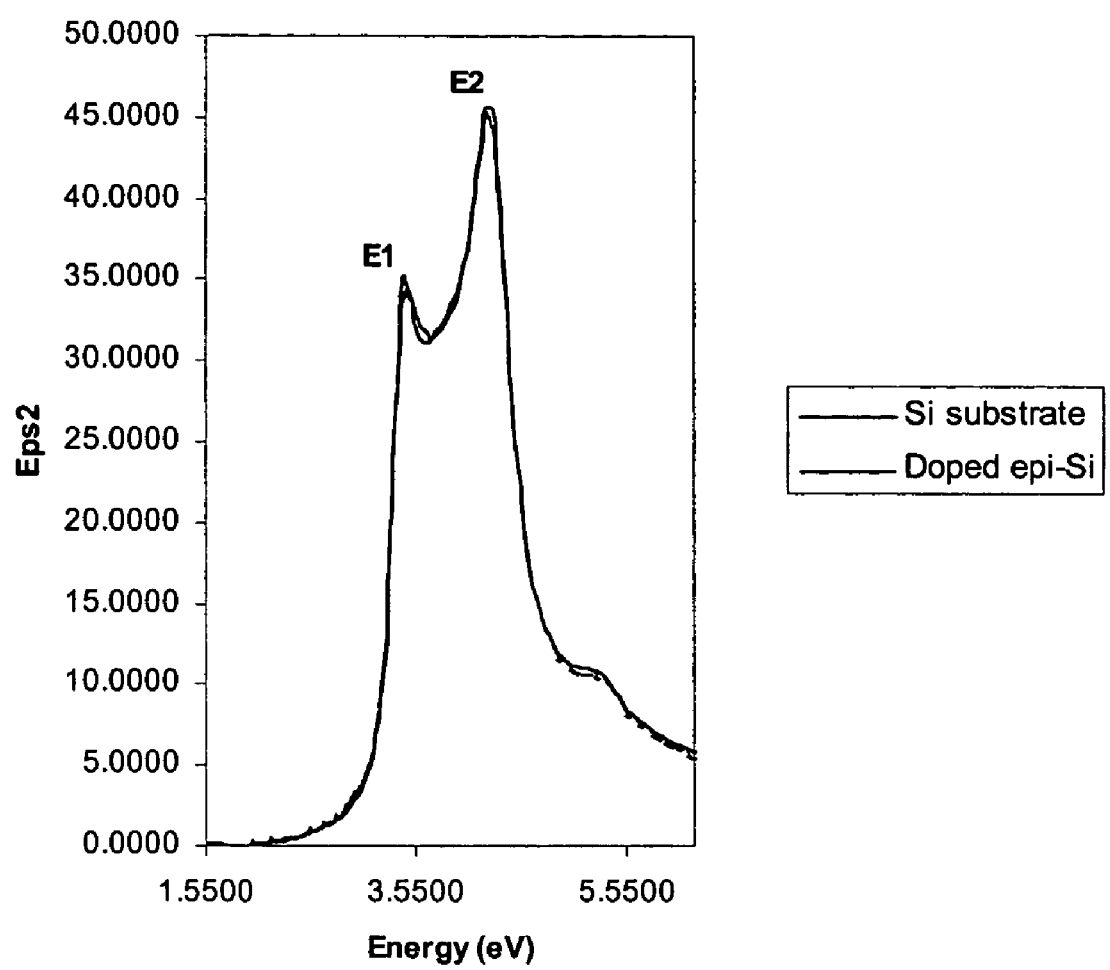
FIG. 1 is a graph showing measured $\epsilon_2$ curves (i.e. values for $\epsilon_2$ plotted as a function of photon energies) for a nominally undoped Silicon substrate and an epitaxially-grown Si film doped with Boron to $\sim 2.5 \times 10^{19}$ cm$^{-3}$, respectively.
Figure 2A:
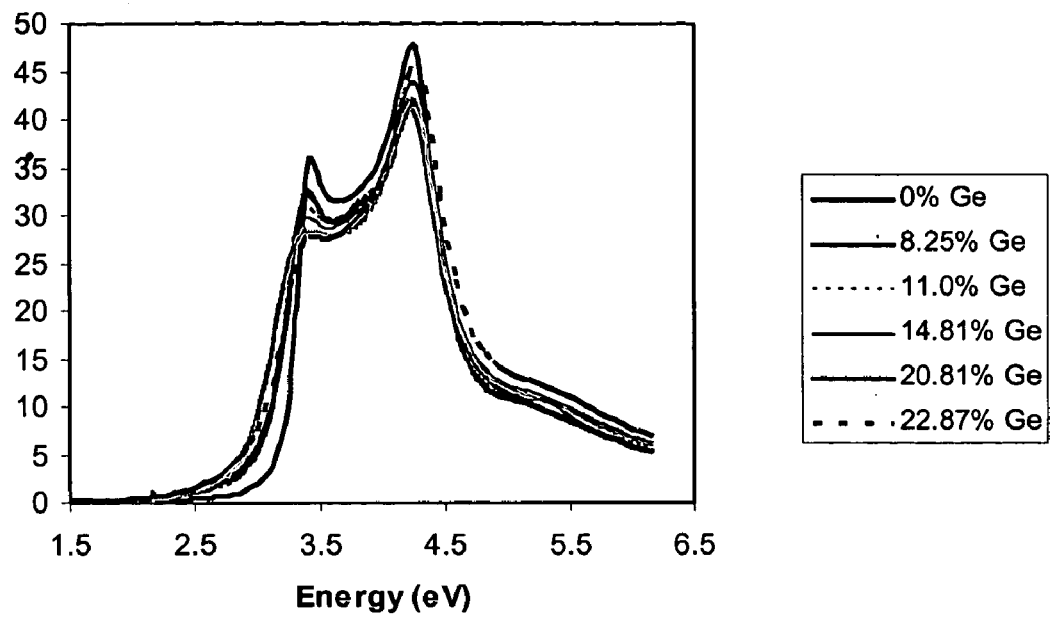
FIG. 2A is a graph showing the measured $\epsilon_2$ curves of a set of nominally undoped epitaxial SiGe films having different Ge fractions ranging from zero to around 23%.
Figure 2B:
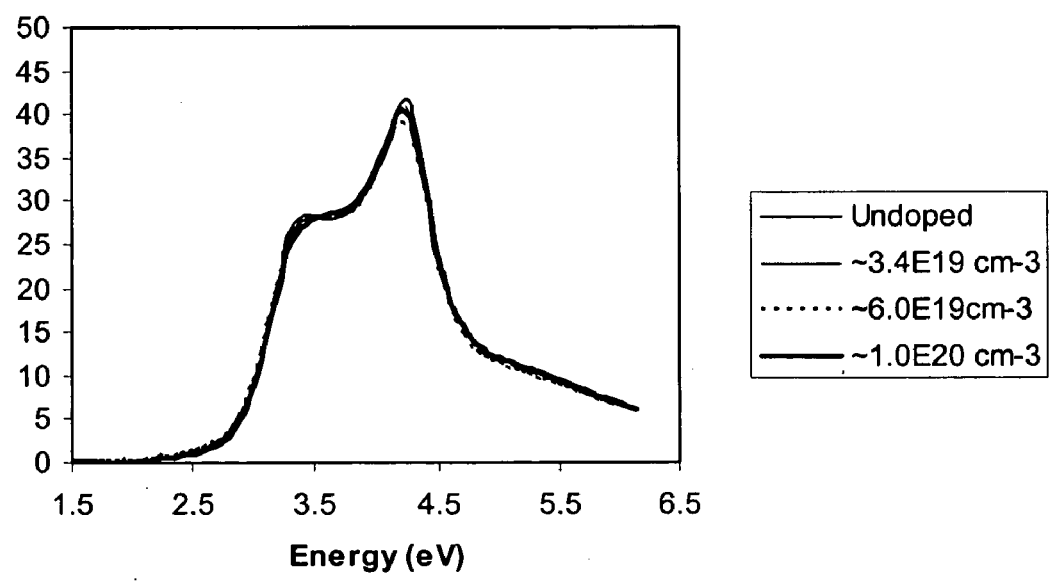
FIG. 2B is a graph showing the measured $\epsilon_2$ curves of a set of epitaxial SiGe films with a nominally constant (21%) Ge fraction but variations in Boron doping level between zero and $1.0 \times 10^{20}$ cm$^{-3}$.

An embodiment of the present invention provides a method for modeling semiconductors that have been modified by doping, strain or quantum confinement. The modeling method starts with an existing model that provides the functions $\epsilon_1(E)$ and $\epsilon_2(E)$ for an unmodified material. The unmodified model may be in any form including lookup table, critical point (CP), effective media approximation (EMA) and others. The functions $\epsilon_{1'}(E)$ and $\epsilon_{2'}(E)$ for the corresponding modified material are defined as superpositions of the functions $\epsilon_1(E)$ and $\epsilon_2(E)$ plus two perturbation functions $\Delta\epsilon_1(E)$ and $\Delta\epsilon_2(E)$. One of three methods (each of which is discussed below) is used to provide a parameterized definition for $\Delta\epsilon_2(E)$. $\Delta\epsilon_1(E)$ is then obtained from $\Delta\epsilon_2(E)$ using the equation (reprinted from above):

$$\Delta\varepsilon_1(E_0) = \int_0^\infty \frac{E\Delta\varepsilon_2(E)}{E^2 - E_0^2} dE \qquad (5)$$

The function $\epsilon_{1'}(E)$ and $\epsilon_{2'}(E)$ (or functions that include $\epsilon_1(E)$ and $\epsilon_2(E)$) are typically used as part of a regression based analysis in which empirically obtained values are compared to values computed using $\epsilon_{2'}(E)$ and $\epsilon_{2'}(E)$. The comparison process is repeated while the parameters to $\Delta\epsilon_2(E)$ are varied until a desired goodness of fit is achieved. At that point, the parameters correspond to the modifications (e.g., doping or strain) applied to the original unmodified material.

In general, solving equation (5) is non-trivial because it is complicated by the presence of a singularity at the point where $E=E_0$ This is true even where the function $\Delta\epsilon_2(E)$ has been defined in such a way as to be zero over most of the energy range. The present invention provides three categories of solutions that address this difficulty: firstly, a general numerical solution for the Kramers-Kronig transform that can transform any arbitrary form for $\Delta\epsilon_2(E)$, together with some examples of such forms; secondly, a mathematical function (the Cauchy distribution) that can conveniently be integrated analytically from zero to infinity; thirdly, an oscillator model that satisfies the Kramers-Kronig condition in its formulation but which is here applied just to the perturbation rather than to the whole dielectric function of the material.

General Numerical Solution

As implied by Zettler et al (see J.-T. Zettler, T. Trepk, L. Spanos, Y.-Z. Hu and W. Richter, "High precision UVvisible-near-IR Stokes vector spectroscopy", Thin Solid Films 234, 402 (1993)), if the function $\Delta\epsilon_2$ is defined at a number of discrete energies $E_1, E_2 \ldots E_n$, then it is possible to represent it analytically by means of a cubic spline whereby in interval k:

$$\Delta\epsilon_2(E) = c_1{}^k + c_2{}^k E + c_3{}^k E^2 + c_4{}^k E^3 \qquad (6)$$

The integral containing $E\Delta\epsilon_2(E)$ can then be done analytically, term by term and interval by interval, using standard integrals by Prudnikov et al (A. P. Prudnikov, Y. A. Brychkov and O. I. Marichev, "Integrals and Series", Gordon and Breach, New York (1986)):

$$\int \frac{E}{E^2 - E_0^2} dE = \frac{1}{2} \log|E^2 - E_0^2| \qquad (7)$$

$$\int \frac{E^2}{E^2 - E_0^2} dE = E - \frac{1}{2} E_0 \log\left|\frac{E + E_0}{E - E_0}\right|$$

$$\int \frac{E^3}{E^2 - E_0^2} dE = \frac{E^2}{2} + \frac{E_0^2}{2} \log|E^2 - E_0^2|$$

$$\int \frac{E^4}{E^2 - E_0^2} dE = \frac{E^3}{3} + E_0^2 \cdot E - \frac{E_0^3}{2} \log\left|\frac{E + E_0}{E - E_0}\right|$$

So long as $\Delta\epsilon_1$ is calculated at a set of energies $E'_1, E'_2 \ldots E'_n$ different from the set $E_1, E_2 \ldots E_n$ at which $\Delta\epsilon_2$ is defined, then no singularities will be encountered; as a final step, $\Delta\epsilon_1$ itself can be represented by a cubic spline in order to derive its values at $E_1, E_2 \ldots E_n$.

With this technique available to do the Kramers-Kronig transform, the function $\Delta\epsilon_2$ can be constructed using any arbitrary functions to achieve suppression/enhancement and/or shifting of the peaks. One such set of functions is described here. In any case, the first step is to identify the positions of the strong features in the $\epsilon_2$ curve, and the procedure is then as follows.

Peak Suppression or Enhancement:

Define an amount of suppression, "S" and a breadth, "B" for the suppression function. At all photon energies that are within half the breadth of the peak position, define a perturbation as:

$$\Delta(E) = \frac{S \times (B - |E - E_{Peak}|)}{B} \qquad (8)$$

Figure 3A:
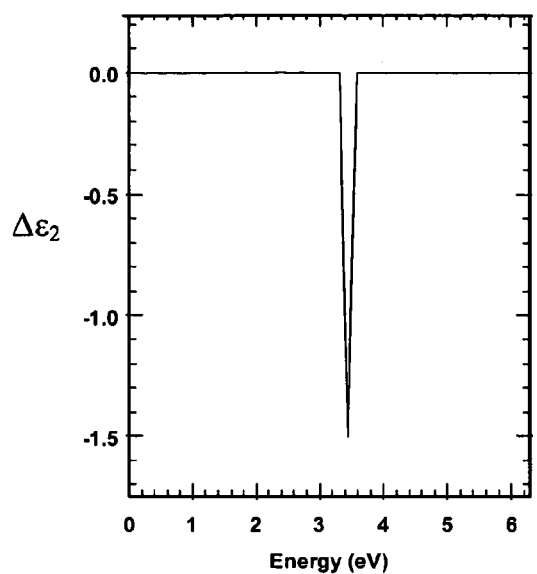
FIG. 3A is a graph showing a peak suppression component of a $\Delta\epsilon_2(E)$ curve as provided by an embodiment of the present invention (equation (8)).
Figure 3B:
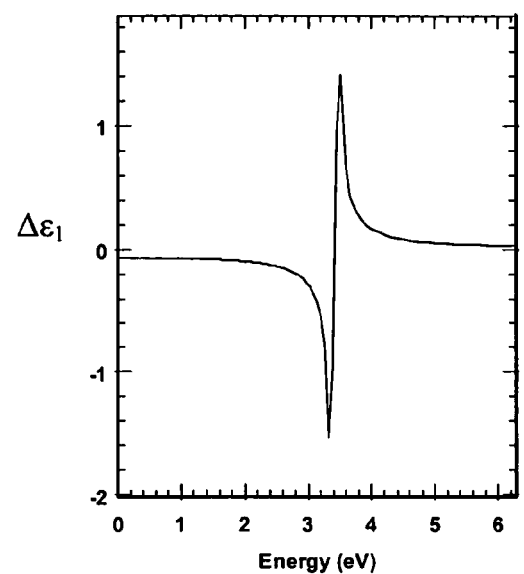
FIG. 3B is a graph showing the corresponding component of $\Delta\epsilon_1(E)$, as obtained by a numerical Kramers-Kronig transform of the curve in FIG. 3A.

This satisfies the condition that the maximum suppression (when $E = E_{peak}$) should be equal to S, and allows S to be negative in which case the peak is enhanced rather than suppressed. FIG. 3A shows an example of the fitting function for S=1.5 and B=0.15. The resulting transform is shown in FIG. 3B.

Peak Shifting:

Define a shift "Sh" and an extent "X". A sinusoidal function is defined such that at energies within "Sh" of the peak, the perturbation is $$\Delta(E) = X \times \sin\left(\frac{E - (E_{Peak} - Sh)}{Sh} \times \pi\right) \qquad (9)$$

Figure 4A:
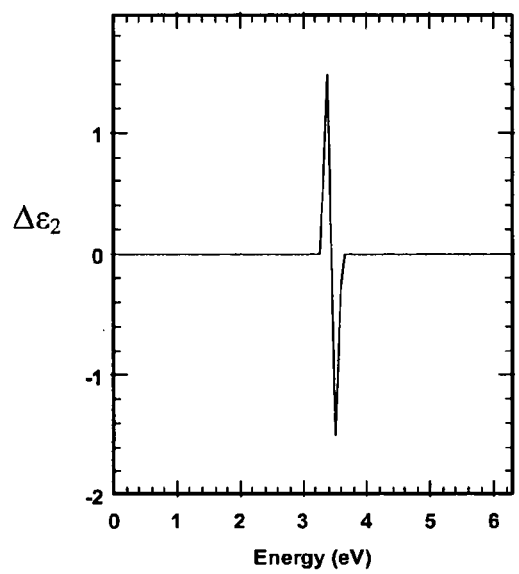
FIG. 4A is a graph showing a peak shifting component of a $\Delta\epsilon_2(E)$ curve as provided by an embodiment of the present invention (equation (9)).
Figure 4B:
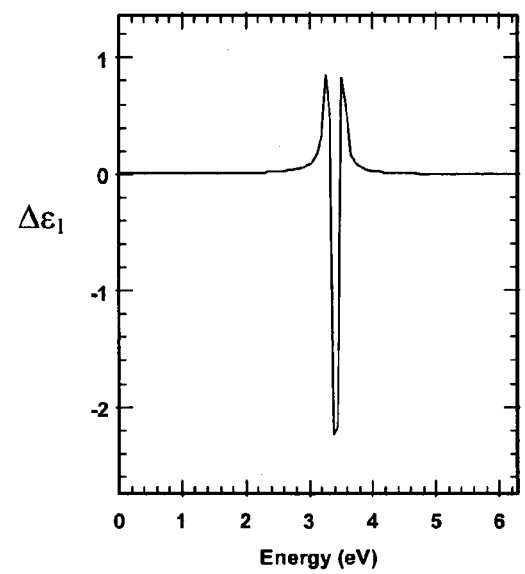
FIG. 4B is a graph showing the corresponding component of $\Delta\epsilon_1(E)$, as obtained by a numerical Kramers-Kronig transform of the curve in FIG. 4A.

FIGS. 4A and 4B show an example of the fitting function, and its resulting transform, when X=1.5 and Sh=0.15.

For a Silicon or SiGe optical function, S, B, Sh and X can be defined for each of the E1 and E2 peaks to obtain a total of eight adjustable parameters.

Cauchy Distribution Solution

A second technique is to find a perturbation function $\Delta\epsilon_2$ with continuous derivatives that can be analytically transformed without having to go through the intermediate stage of conversion to a cubic spline. These criteria are satisfied by the Cauchy distribution which is generally written in the form:

$$\Delta\epsilon_2(E) = \frac{C}{\pi \cdot B \cdot \left[1 + \left(\frac{E - A}{B}\right)^2\right]} \qquad (10)$$

where A represents the position of the peak, B represents the breadth of the distribution and C is a scaling factor.

Figure 5A:
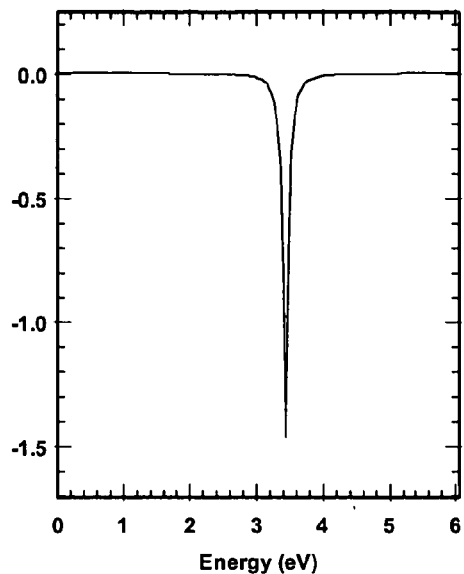
FIG. 5A is a graph showing the Cauchy Distribution model (equation (10) with C<0) applied as a peak suppression function in $\Delta\epsilon_2(E)$.

As shown in FIG. 5A, the overall shape of the Cauchy distribution is suitable for peak suppression in the $\epsilon_2$ curve. It is also smooth and continuously differentiable. This contrasts to the equation used for peak suppression used within the cubic spline solution (i.e. equation (8)). It also has the virtue (unlike, for example, the normal distribution, the Laplace distribution or numerous similar functions) that its Kramers-Kronig transform:

$$\Delta\epsilon_1(E_0) = \int_0^\infty \frac{C}{\pi \cdot B \cdot \left[1 + \left(\frac{E - A}{B}\right)^2\right]} \cdot \frac{E}{E^2 - E_0^2} dE \qquad (11)$$

has a closed analytical form, viz.

$$\Delta\epsilon_1(E_0) = -\frac{C}{2\pi} \cdot \frac{\left(\begin{array}{l} A \cdot (E_0^2 - A^2 - B^2) \cdot \left(\pi + 2\tan^{-1}\left(\frac{A}{B}\right)\right) + \\ B \cdot (E_0^2 + A^2 + B^2) \cdot (2 \cdot \log(E_0) - \log(A^2 + B^2)) \end{array}\right)}{(E_0^2 + 2AE_0 + A^2 + B^2)(E_0^2 - 2AE_0 + A^2 + B^2)} \qquad (12)$$

Figure 5B:
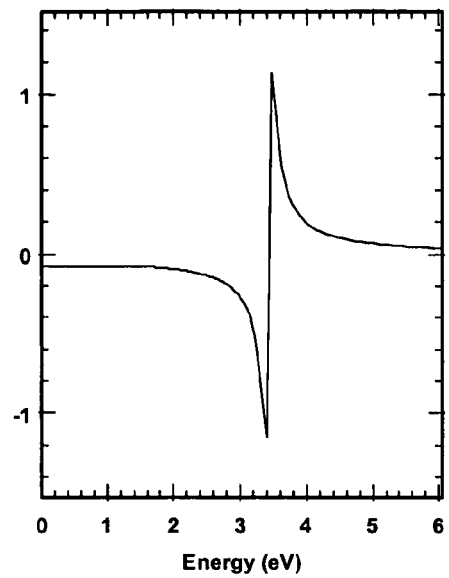
FIG. 5B is the corresponding component of $\Delta\epsilon_1(E)$, obtained by an analytical Kramers-Kronig transform as shown in equation (12).

As a result, it is not necessary to use the cubic spline method described previously to perform the Kramers-Kronig transform. The function is straightforwardly calculated as shown in FIG. 5B.

Figure 6A:
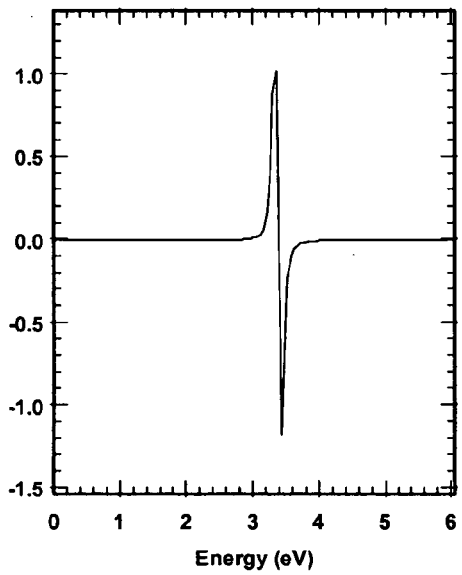
FIG. 6A is a graph showing how two Cauchy distribution functions with opposite signs may be combined to form a shifting function analogous to FIG. 4A.
Figure 6B:
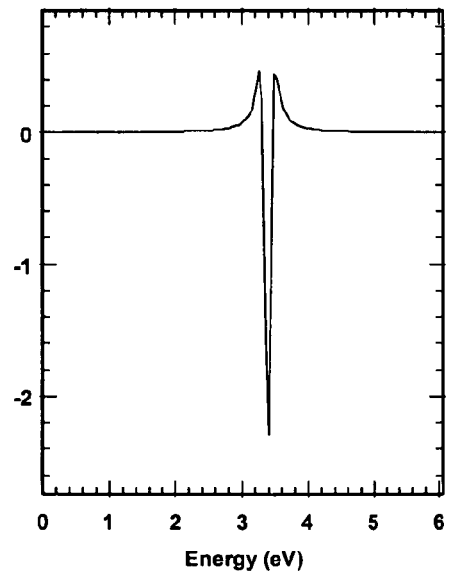
FIG. 6B is the corresponding analytical Kramers-Kronig transform.
Figure 7A:
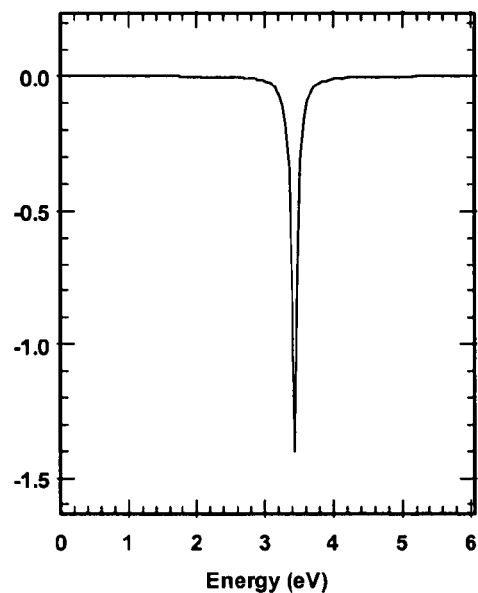
FIG. 7A is a graph showing a single harmonic oscillator applied as a peak suppression function in $\Delta\epsilon_2(E)$.
Figure 7B:
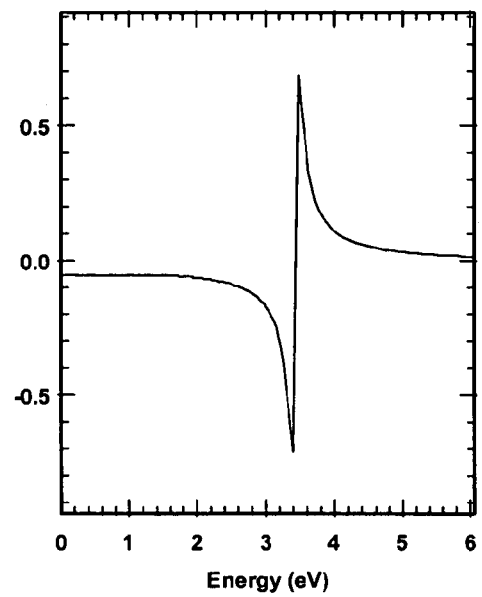
FIG. 7B is the corresponding component of $\Delta\epsilon_1(E)$.
Figure 8A:
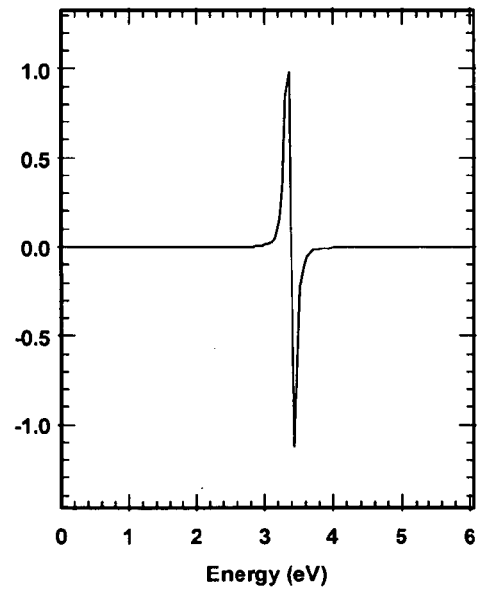
FIG. 8A is a graph showing how two harmonic oscillators with opposite signs may be combined to form a shifting function analogous to FIG. 4A.
Figure 8B:
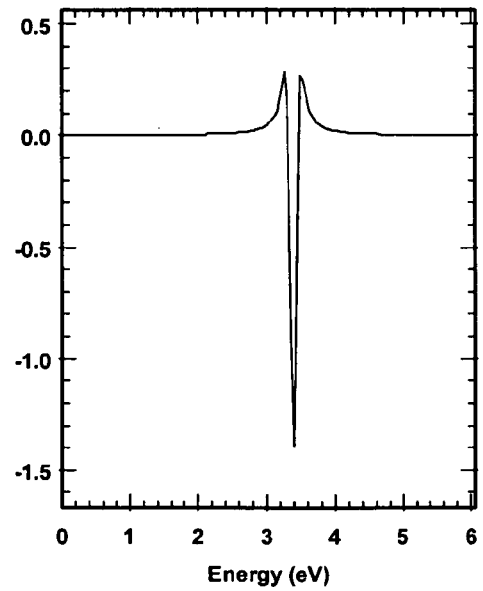
FIG. 8B is the corresponding component of $\Delta\epsilon_1(E)$.

As noted, the Cauchy distribution is most easily applied to perform peak suppression or enhancement. To perform peak shifting, two different approaches are possible. The first is to use the previously described sinusoidal function (equation (9)) and resort to the numerical Kramers-Kronig technique. The second is to use a combination of separate Cauchy distributions. Typically, this involves two slightly shifted distributions, one positive and the other negative, as shown in FIG. 6A. The use of the separate Cauchy distributions retains the advantage that the Kramers-Kronig transform is directly integrable without the use of a cubic spline function: the result of such an analytical integration is shown in FIG. 6B.

Oscillator Solution

A third technique is to model the perturbation functions $\Delta\epsilon_1$ and $\Delta\epsilon_2$ simultaneously using an oscillator model that is Kramers-Kronig consistent by design. Any oscillator model that meets this requirement is suitable for this purpose. FIGS. 7A through 8B, which correspond to the cases described for 5A to 6B, were obtained using the simplest possible harmonic oscillator model:

$$\Delta\varepsilon_1(E) + i\Delta\varepsilon_2(E) = \frac{C}{E - A + iB} - \frac{C}{E + A + iB} \quad (13)$$

EXAMPLES

Example A

Figure 9A:
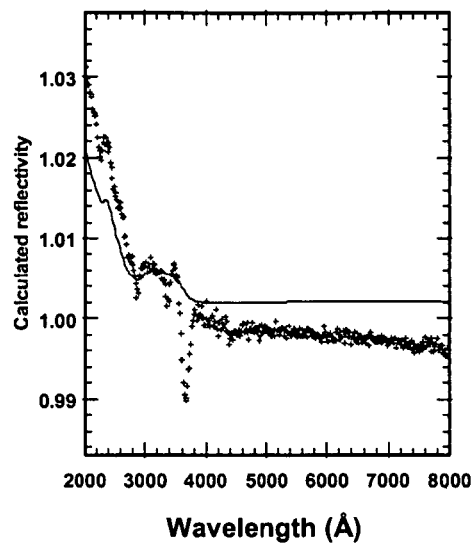
FIGS. 9A through 9C are an example showing application of the peak suppression and peak shifting functions (similar to those shown in FIGS. 2 and 3) to lookup-table $\epsilon_2$ curves for a crystalline Silicon sample.
Figure 9B:
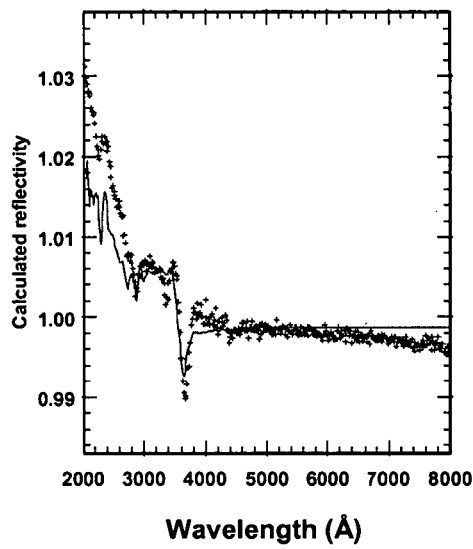
Figure 9C:
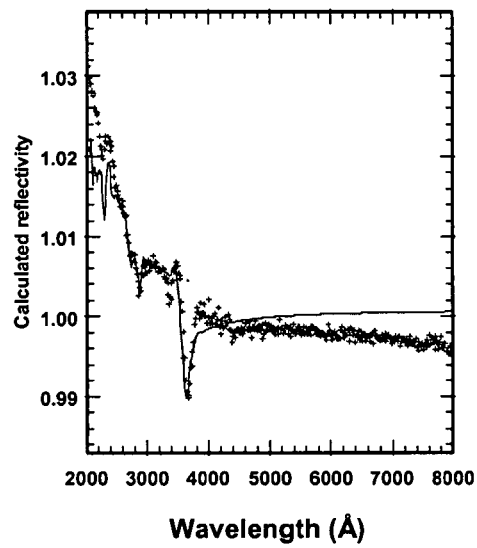

A set of data from a doped epitaxial substrate: there was said to be ~600 Å of doped Si on a standard crystalline substrate, but the total lack of interference fringes in the data indicates that there is no interface close to the surface. For the purposes of the exercise, it is assumed that the whole substrate is doped. FIG. 9A shows the spectrum obtained using a crystalline Si lookup-table model. Note, the sharp feature at ~3700 Å corresponding to the E1 peak energy of ~3.4 eV. After applying the two-parameter suppression function described in equation (8), the results of FIG. 9B are obtained. Not only is the sharp feature at ~3700 Å now accurately fitted, but the fit has also improved over the whole wavelength range with the possible exception of the DUV below 3000 Å. This can be taken one step further by adding a shift function as described in equation (9) and performing a similar perturbation upon the E2 peak. The result is shown in FIG. 6C.

Example B

Figure 10A:
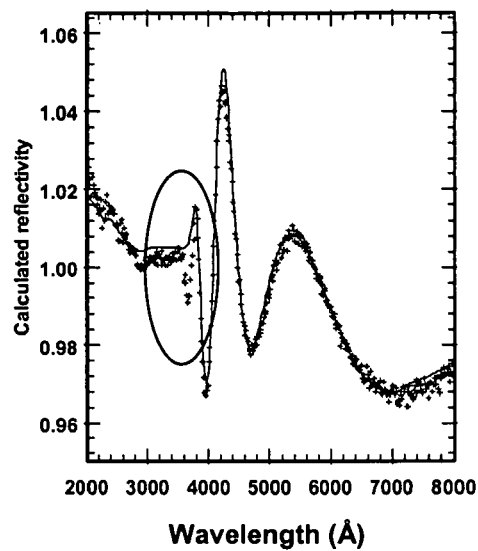
FIGS. 10A through 10C are an example showing application of the peak suppression and peak shifting functions to EMA-modeled $\epsilon_2$ curves for a SiGe sample.
Figure 10B:
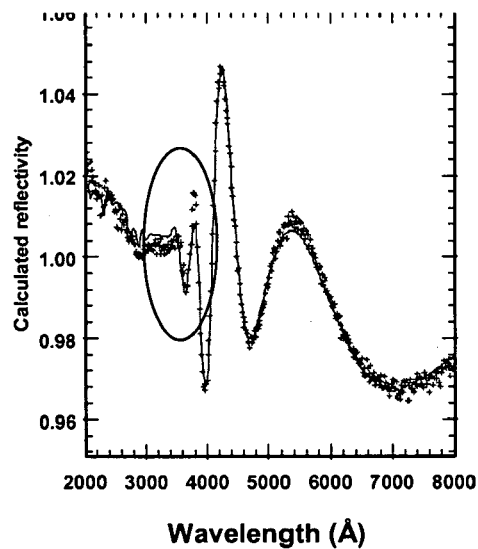
Figure 10C:
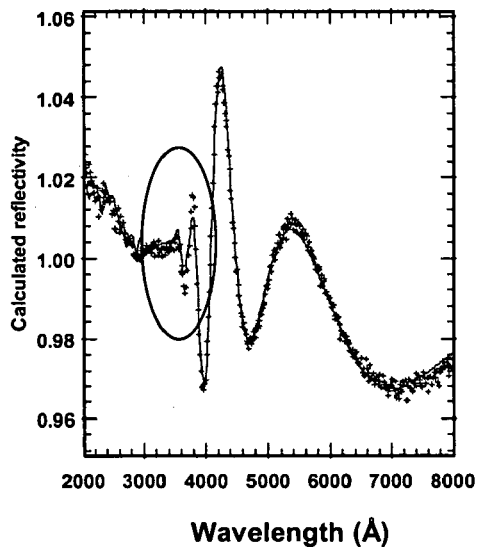
Figure 11A:
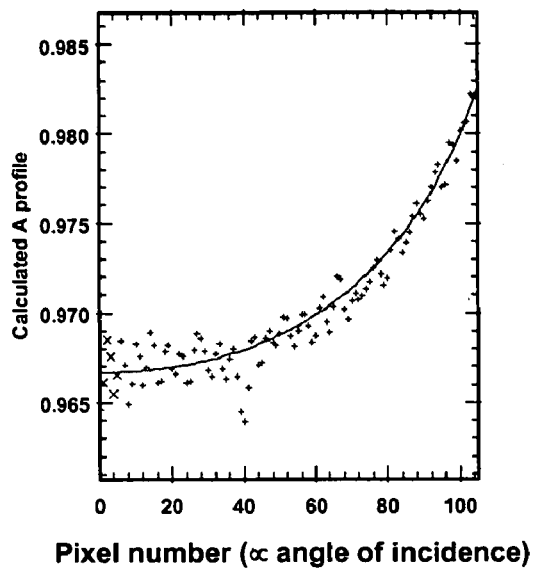
FIGS. 11A through 11E show the fits obtained to Beam Profile Reflectometry, Spectrophotometry and Spectroscopic Ellipsometry curves for a nominally undoped SiGe layer under a nominally undoped epitaxial Si cap.
Figure 11B:
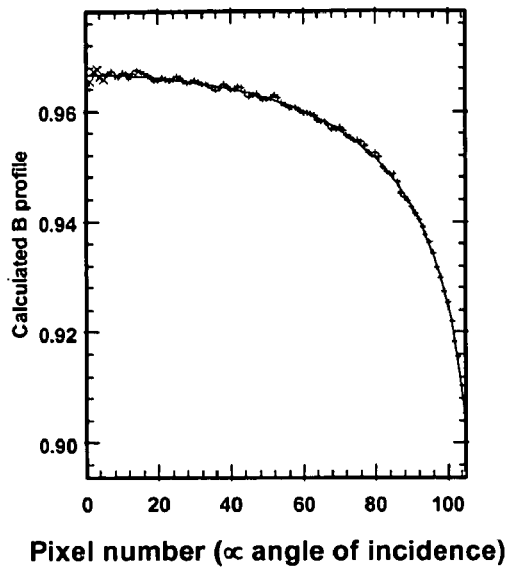
Figure 11C:
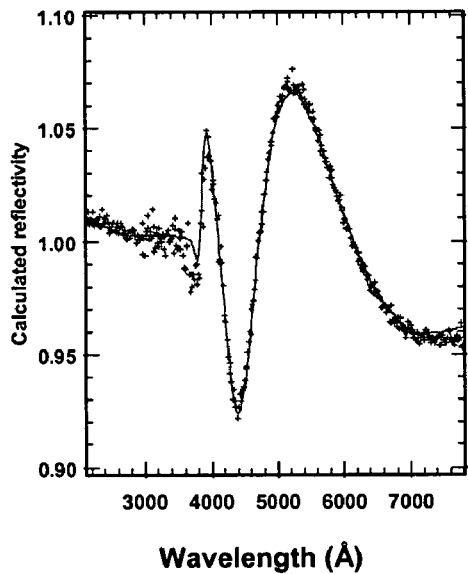
Figure 11D:
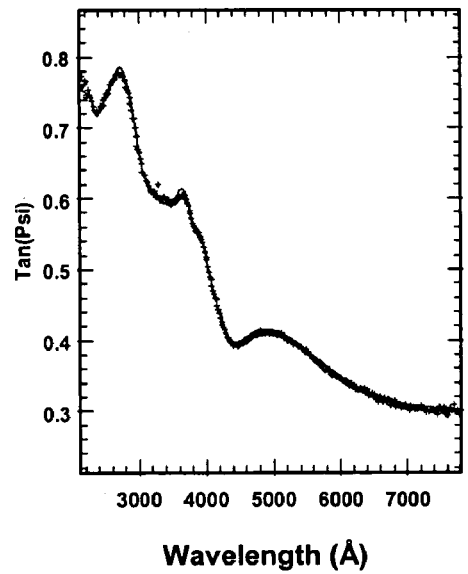
Figure 11E:
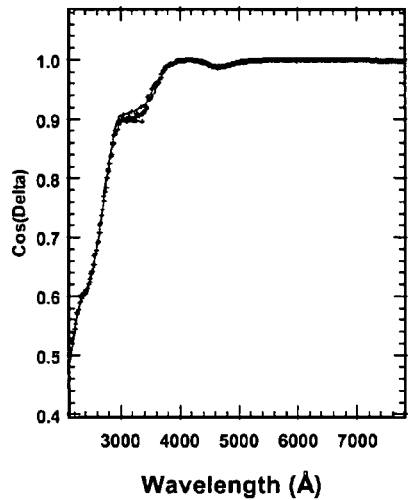
Figure 12A:
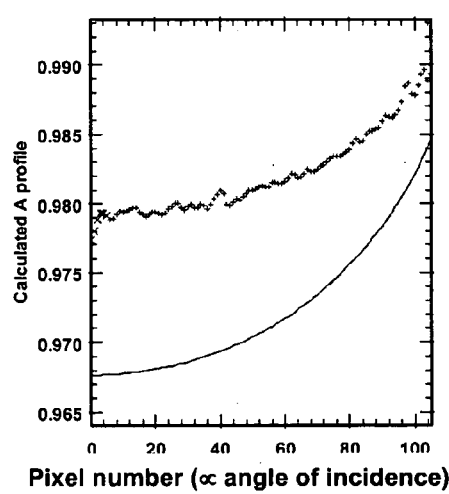
FIGS. 12A through 12E show the corresponding fits obtained for a Boron-doped SiGe layer under a nominally undoped epitaxial Si cap, if the doping of the SiGe is not explicitly accounted for in the model.
Figure 12B:
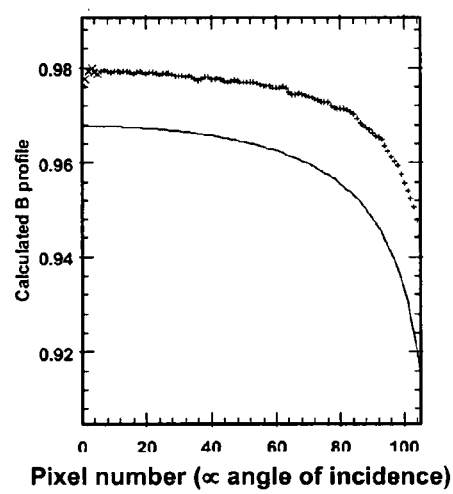
Figure 12C:
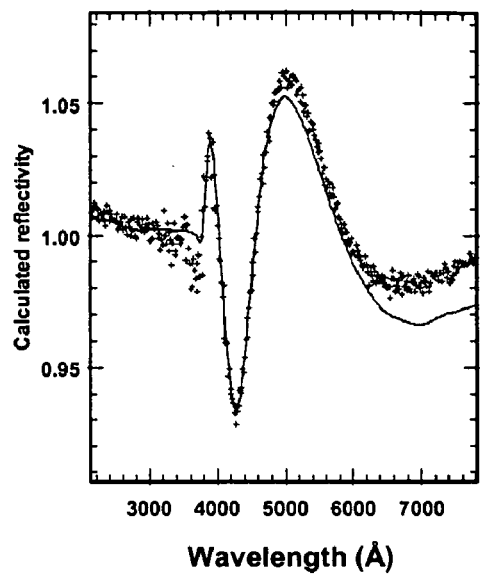
Figure 12D:
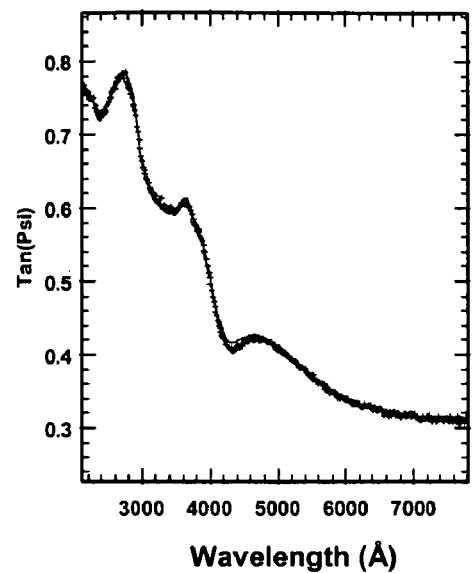
Figure 12E:
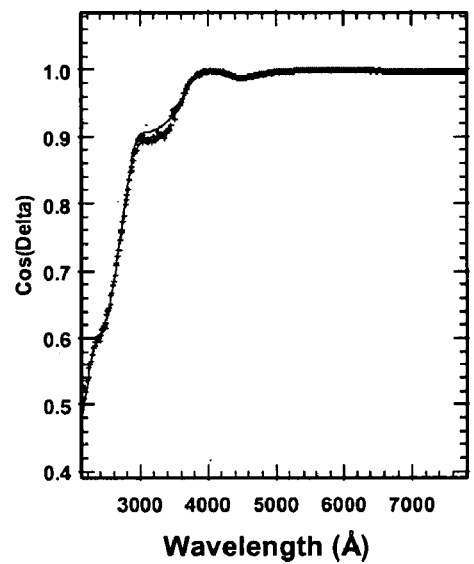
Figure 13A:
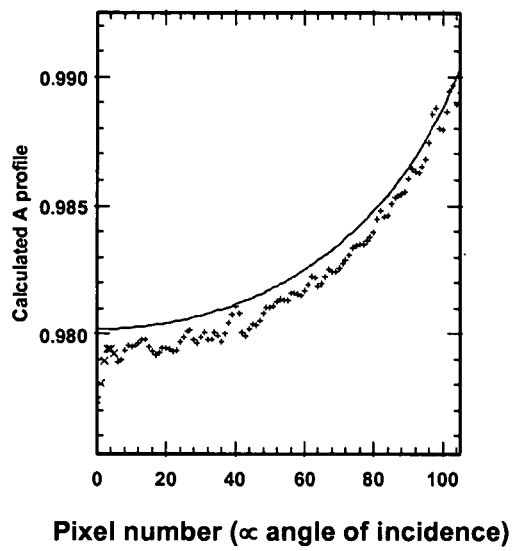
FIGS. 13A through 13E show the corresponding fits obtained from the same sample as in FIGS. 12A through 12E, when the doping of the SiGe is explicitly accounted for by the present invention.
Figure 13B:
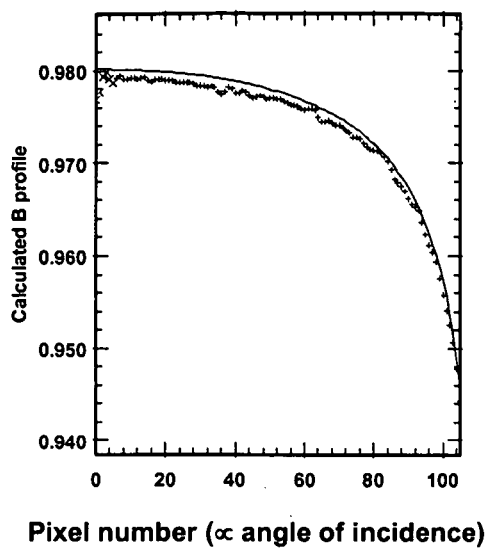
Figure 13C:
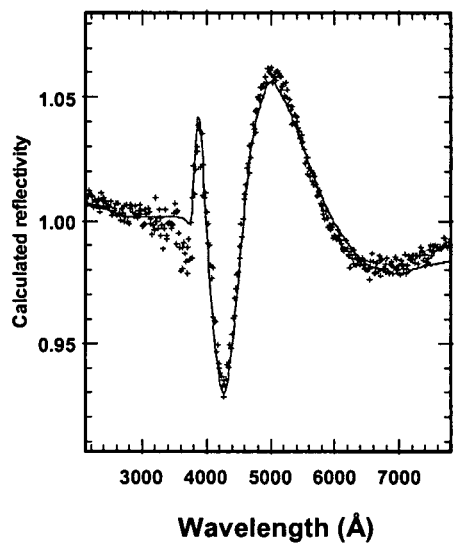
Figure 13D:
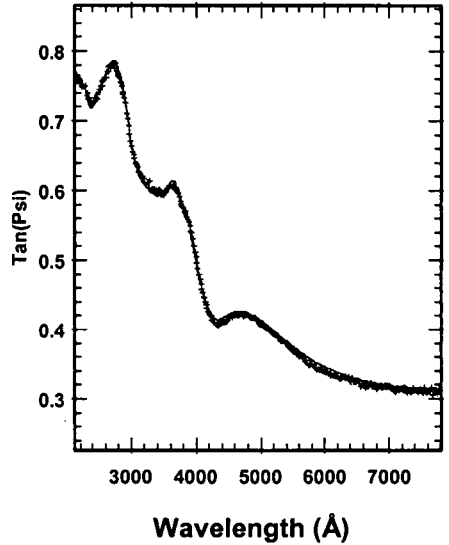
Figure 13E:
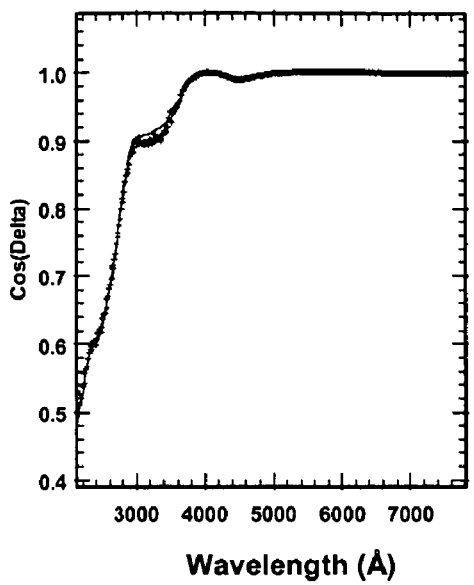

FIGS. 10A through 10C show the same sort of application applied to representative data from an undoped SiGe layer under a doped Si cap. In this case, the dispersion of the cap is modified rather than the SiGe itself. FIG. 10A shows the fit to the data obtained when using a standard c-Si lookup table to represent the cap, FIG. 10B shows the fit obtained using the doped-Si model derived above, and FIG. 10C shows the result of doing a complete optimization using the data point itself. Note how, with the doping model, a good fit is obtained for the feature at ~3800 Å (circled) which is completely missed by the c-Si model.

Example C

FIGS. 11A through 11E show the fits obtained for several of the optical technologies available on the Opti-Probe tool from an undoped $Si_{0.82}Ge_{0.18}$ layer under an undoped cap; as can be seen, the fit to all technologies is very good. In FIGS. 12A through 12E, the corresponding data from a similar wafer with a doped SiGe layer is shown, as fitted using the same recipe that did not allow for the presence of doping. The large errors in the fit clearly indicate the dangers of leaving doping unaccounted for. FIGS. 13A through 13E show the results of applying the present invention to the same data, and shows that all of the technologies can simultaneously be brought into good agreement.

Example D

Figure 14:
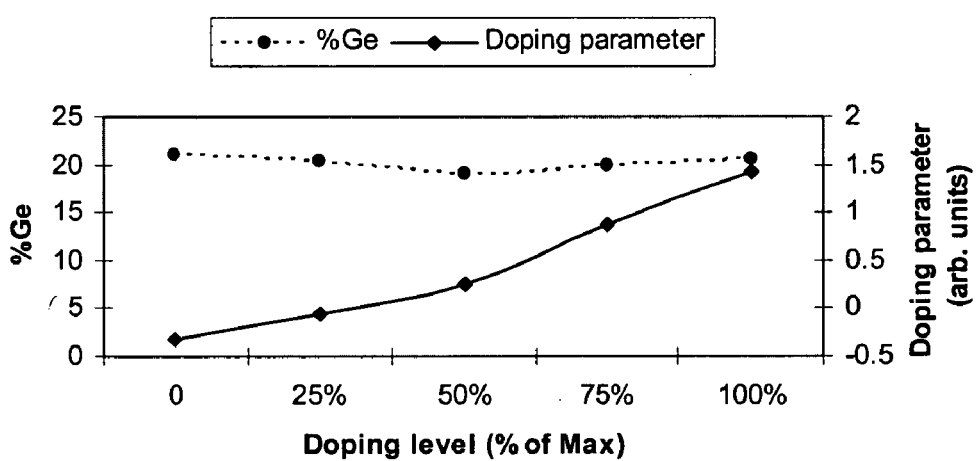
FIG. 14 shows the results of a simultaneous measurement by means of the present invention of Ge fraction and Boron doping level for a set of doped epitaxial SiGe films with nominally 21% Ge.

FIG. 14 shows plots of Ge-fraction and E1 suppression ("C" in equation (11)) for a set of single-layer SiGe films on Si which had nominally constant Ge-fraction but varying Boron levels as shown (the x-axis shows percentages of the maximum doping, which was here $1.0 \times 10^{20}$ cm$^{-3}$). This shows that the present invention is indeed applicable for the simultaneous measurement of Ge-fraction and doping level.

What is claimed is:

1. A method for optically evaluating a sample, the method comprising:

defining a parameterized $\Delta\in_2$ perturbation function to represent the difference between the $\in_2'$ dispersion curve of the sample and the $\in_2$ dispersion curve of a similar sample having a known dopant concentration;

defining a $\Delta\in_1$ perturbation function to represent the difference between the $\in_1'$ dispersion curves of the sample and the similar sample having a known dopant concentration, where the $\Delta\in_1$ perturbation function is defined as a Kramers-Kronig transform upon the $\Delta\in_2$ perturbation function;

illuminating the sample with a probe beam; and detecting the reflected probe beam and generating output signals wherein said output signals can be compared to the $\Delta\in_2$ and $\Delta\in_1$ perturbation functions for evaluating the sample.

2. A method as recited in claim 1 that further comprises:

applying a general function to perturb the strong features of the $\in_2$ curve of the similar sample;

representing the $\Delta\in_2$ perturbation curve as a cubic spline function;

performing a Kramers-Kronig transformation by integrating the cubic spline function to obtain a corresponding $\Delta\in_1$ curve; and combining the perturbations upon $\in_1$ and $\in_2$ curves to obtain a new dielectric function and hence n and k curves for the sample.

3. A method as recited in claim 1 that further comprises:

applying a Cauchy distribution function to perturb the strong features of the $\in_2$ curve of the similar sample;

performing a Kramers-Kronig transformation by directly integrating the Cauchy distribution function curve to obtain a corresponding $\in_1$ perturbation curve; and combining the perturbations upon $\in_1$ and $\in_2$ curves to obtain a new dielectric function and hence n and k curves for the sample.

4. A method as recited in claim 1 that further comprises:

constructing a Kramers-Kronig consistent oscillator model; and obtaining the perturbation functions for the $\in_1$ and $\in_2$ curves as respectively the real and imaginary parts of the oscillator model.

5. An apparatus for optically evaluating a sample, the apparatus comprising:

an illumination source for generating a probe beam;

one or more optical components for directing the probe beam at the sample and for gathering the reflected probe beam;

a detector for converting the reflected probe beam into corresponding signals;

a processor for analyzing the signals to determine the optical dispersion of the sample, the processor configured to:

represent the difference between the $\in_2'$ dispersion curve of the sample and the $\in_2$ dispersion curve of a similar sample having a known dopant concentration using a parameterized $\Delta\in_2$ perturbation function;

represent the difference between the $\in_1$ dispersion curves of the sample and the similar sample having a known dopant concentration using a $\Delta\in_1$ perturbation function, where the $\Delta \in_1$ perturbation function is defined as a Kramers-Kronig transform upon the $\Delta \in_2$ perturbation function; and repeatedly evaluating the $\Delta \in_2$ perturbation function against the signals while changing the parameters in order to find the correct dispersion curve for the sample and, by inference from the best-fit parameters, the dopant concentration of the sample.

6. An apparatus as recited in claim 5 in which the processor is configured to:

apply a general function to perturb the strong features of the $\in_2$ curve of the similar sample;

represent the $\Delta \in_2$ perturbation curve as a cubic spline function;

perform a Kramers-Kronig transformation by integrating the cubic spline function to obtain a corresponding $\Delta \in_1$ curve; and combine the perturbations upon $\in_1$ and $\in_2$ curves to obtain a new dielectric function and hence n and k curves for the sample.

7. An apparatus as recited in claim 5 in which the processor is configured to:

apply a Cauchy distribution function to perturb the strong features of the $\in_2$ curve of the similar sample;

perform a Kramers-Kronig transformation by directly integrating the Cauchy distribution function curve to obtain a corresponding $\in_1$ perturbation curve; and combine the perturbations upon $\in_1$ and $\in_2$ curves to obtain a new dielectric function and hence n and k curves for the sample.

8. An apparatus as recited in claim 5 in which the processor is configured to:

construct a Kramers-Kronig consistent oscillator model; and obtain the perturbation functions for the $\in_1$ and $\in_2$ curves as respectively the real and imaginary parts of the oscillator model.

* * * * *